US00PP24688P2

(12) United States Plant Patent
Saul et al.

(10) Patent No.: US PP24,688 P2
(45) Date of Patent: Jul. 22, 2014

(54) ***COREOPSIS* 'ELECTRIC AVENUE'**

(50) Latin Name: *Coreopsis verticillata*
Varietal Denomination: Electric Avenue

(71) Applicants: Richard G. Saul, Cleveland, GA (US); Patricia M. Bauer, Lucinda, PA (US)

(72) Inventors: Richard G. Saul, Cleveland, GA (US); Patricia M. Bauer, Lucinda, PA (US)

(73) Assignee: Itsaul Plants, LLC, Alpharetta, GA (US)

( * ) Notice: Subject to any disclaimer, the term of this patent is extended or adjusted under 35 U.S.C. 154(b) by 110 days.

(21) Appl. No.: 13/573,637

(22) Filed: Sep. 27, 2012

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of *Coreopsis verticillata* named 'Electric Avenue' characterized by its inflorescences that are clear yellow in color, its thread-leaf foliage, its high bud count, its height of 60 to 71 cm and an average spread of 60 cm, its cold hardiness in at least U.S.D.A. Zone 5, and its vigorous growth habit with heavy shoot production from over-wintered plants.

2 Drawing Sheets

Botanical classification: *Coreopsis verticillata.*
Variety denomination: 'Electric Avenue'.

BACKGROUND OF THE INVENTION

The present invention relates to a new and distinct cultivar of *Coreopsis* plant, botanically known as *Coreopsis verticillata* 'Electric Avenue' and will be referred to hereinafter by its cultivar name, 'Electric Avenue'. The new cultivar of *Coreopsis* is an herbaceous perennial grown for landscape and container use.

The new invention arose as a naturally occurring branch plant mutation of *Coreopsis* 'Route 66' (U.S. Plant Pat. No. 20,609) that was growing in a container in Alpharetta, Ga. in summer of 2009.

Asexual reproduction of the new cultivar was first accomplished by stem tip cuttings under the direction of one of the Inventors in Alpharetta, Ga. in the summer of 2009. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Electric Avenue' as unique from all *Coreopsis* cultivars known to the Inventors.

1. 'Electric Avenue' exhibits inflorescences that are clear yellow in color and consistent spring through fall.
2. 'Electric Avenue' exhibits thread-leaf foliage (typical of *C. verticillata*).
3. 'Electric Avenue' exhibits a high bud count.
4. 'Electric Avenue' has shown to be cold hardy at least in U.S.D.A. Zone 5.
5. 'Electric Avenue' exhibits a height of 60 to 71 cm (24 to 28 inches) and an average spread of 60 cm (24 inches).
6. 'Electric Avenue' exhibits a vigorous growth habit with heavy shoot production from over-wintered plants.

'Route 66', the parent plant of 'Electric Avenue' differs from 'Electric Avenue' in having ray florets that are paler yellow with a red eye. 'Electric Avenue' can be most closely compared to *Coreopsis* 'Zagreb' (not patented) and *Coreopsis* 'Moonbeam' (not patented). 'Zagreb' is similar to 'Electric Avenue' in having the same dense growth habit with *C. verticillata* type foliage and a high stem count. 'Zagreb' differs from 'Electric Avenue' in having clear golden yellow ray florets that are shorter in length and more pointed, in being 15 cm (6 inches) shorter in height and in requiring supplemental lighting for winter propagation. 'Moonbeam' is similar to 'Electric Avenue' in having *C. verticillata* type foliage. 'Moonbeam' differs from 'Electric Avenue' in having ray florets that are paler yellow in color and shorter in length, in having a more open plant habit with a lower stem count per plant and in being shorter in height.

BRIEF DESCRIPTION OF THE DRAWING

The accompanying colored photographs illustrate the overall appearance and distinct characteristics of the new *Coreopsis* as grown in Alpharetta, Ga. The photographs were taken of plants about one year in age as grown in a 2-gallon container without deadheading.

The photograph in FIG. 1 provides a side view of 'Electric Avenue' in bloom.

Figure 1:
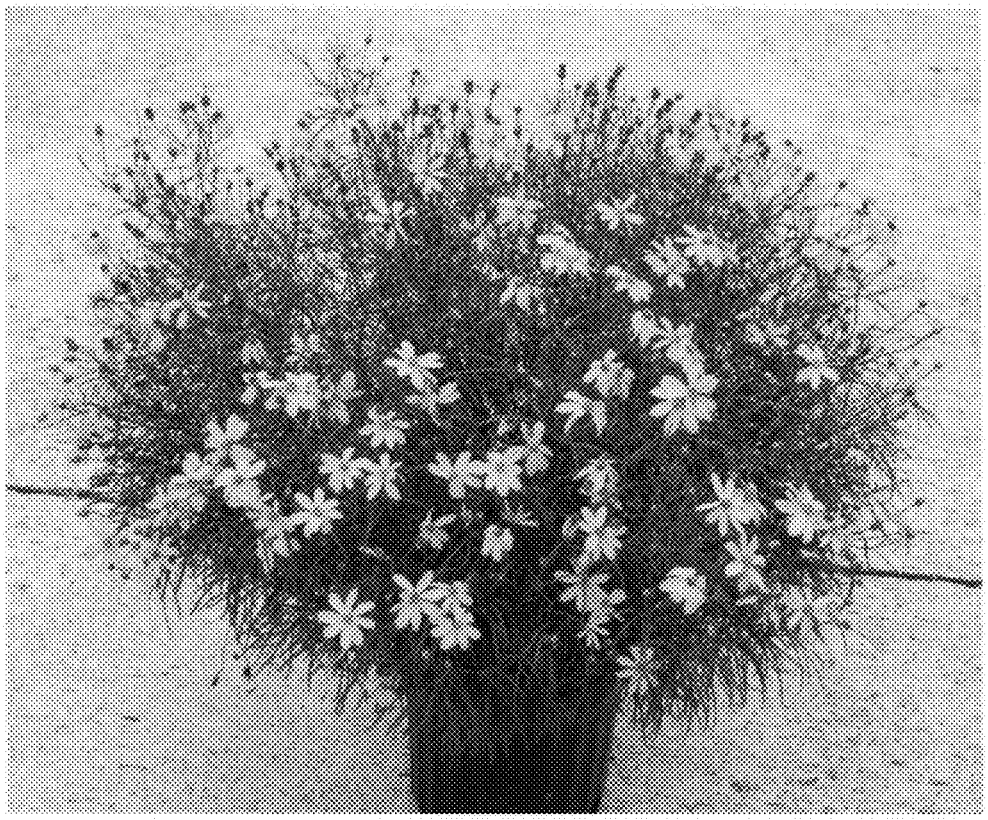
Figure 2:
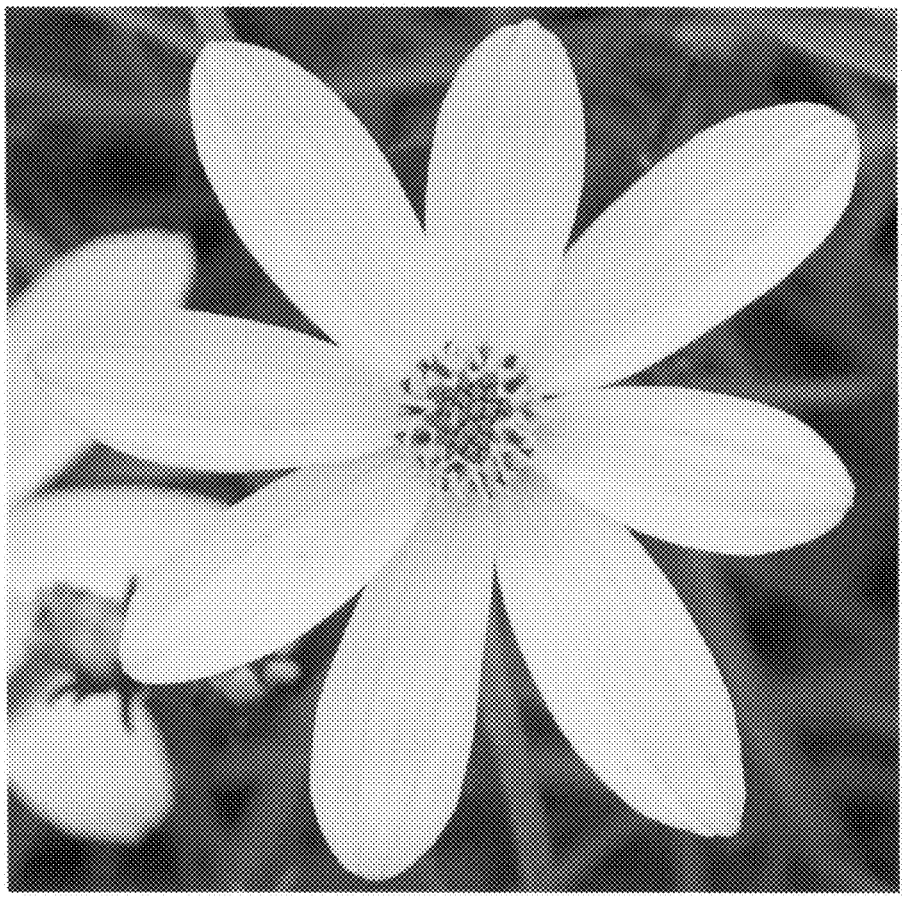

The photograph in FIG. 2 provides a close-up view of an inflorescence of 'Electric Avenue'.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed on plants about one year in age as grown in 2-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*.—Continuous blooms May through September in Alpharetta, Ga.

*Plant habit.*—Herbaceous perennial, densely clump-forming with numerous basal branching to produce a bushy habit.

*Height and spread.*—Reaches a height of 60 to 71 cm (24 to 28 inches) and an average spread of 60 cm (24 inches).

*Cold hardiness.*—At least in U.S.D.A Zone 5.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous with heavy shoot production from overwintered plants without the need for supplemental lighting in winter.

Stem description:

*Shape.*—Oval, solid.

*Stem color.*—144A.

*Stem size*—An average of 34 cm in length (to the bottom of the inflorescence) and 2 mm in width.

*Stem surface.*—Glabrous, satin finish, slightly ridges.

*Branching habit.*—An average of 70 basal branches.

Foliage description:

*Leaf division.*—Simple.

*Leaf margins.*—Deeply incised with an average of 5 lobes.

*Leaf size.*—Up to 8 cm in length and 5 cm in width, lobes an average of 2.5 cm in length and 2 mm in width.

*Leaf shape.*—Fan shaped overall, lobes narrowly linear (thread-like).

*Leaf base.*—Attenuate.

*Leaf apex.*—Acute.

*Leaf venation.*—Pinnate, not prominent, matches leaf color on both surfaces.

*Leaf attachment.*—Sessile.

*Leaf arrangement.*—Opposite.

*Leaf internode length.*—Average of 4.5 cm.

*Leaf quantity.*—An average of 12 per stem.

*Leaf surface.*—Glabrous.

*Leaf color.*—New growth upper and lower surface; 144A, mature leaves upper and lower surface; 137A.

*Leaf fragrance.*—Faint and slightly mint-like when crushed.

Flower description:

*Inflorescence type.*—Composite with ray florets surrounding disk florets in the center forming a radiant head, borne at upper nodes and terminus.

*Lastingness of inflorescence.*—About one week until senescence of ray flowers, bracts and disk flowers are persistent.

*Fragrance.*—None detected.

*Quantity of inflorescences.*—An average of 8 per stem open at one time but continuously produced from May through September.

*Inflorescence size.*—An average of 1 cm in depth and up to 5 cm in width with disk portion an average of 7 mm in diameter.

*Inflorescence buds.*—Average of 5 mm in depth and 4 mm in width, shape is squared oblate, color is 153A with base 137B and apex 153B.

*Peduncle.*—Average of 5 cm in length and 1 mm in diameter, 137C in color, glabrous surface.

Involucral bracts:

*Bract number.*—Two rows of 8 typically.

*Bract arrangement.*—Outer bracts are un-fused spreading and held at 45° from perpendicular, inner bracts overlap and surround receptacle with a campanulate form and held close to ray florets with apical portion spreading outward.

*Bract size.*—Outer bracts about 5 mm in length and 1 mm in width, inner bracts about 7 mm in length and 4 mm in width with free portion an average of 4 mm in length and 3 mm in width.

*Bract color.*—Outer bracts 137A with thin margin of 145A (both surfaces), inner bracts 137A and blending to 153A at apex (both surfaces).

*Bract texture.*—Outer bracts glabrous and satiny on both surfaces, inner bracts glabrous and waxy on both surfaces.

*Bract apex.*—Acute (inner and outer).

*Bract base.*—Truncate (inner and outer).

*Bract shape.*—Outer bracts linear, inner bracts broadly ovate.

Ray florets (sterile):

*Number.*—8.

*Shape.*—Oblong.

*Size.*—Average of 2.5 cm in length and 8 mm in width.

*Apex.*—Broadly acute and slightly 2-notched.

*Base.*—Cuneate.

*Margins.*—Entire.

*Aspect.*—Held nearly horizontal.

*Surface.*—Glabrous and ridged on both surfaces.

*Color.*—Upper surface opening and fully open; 7A, lower surface opening and fully open; 6A.

Disk flowers (male and female):

*Number.*—Numerous, about 80.

*Shape.*—Tubular, corolla is fused, flared at apex.

*Size.*—About 4 mm in length and 1 mm in width.

*Color.*—In masse: base; 12A, with stigmas 200B, corolla; 11C and apex 23A.

*Receptacle.*—About 2 mm in diameter and 2 mm in depth, 137B in color.

Reproductive organs:

*Presence.*—Disk flowers are perfect, ray flowers are sterile.

*Gynoecium.*—1 Pistil, 6 mm in length, style is very fine and about 14B in color and translucent, bifid pilose stigma is 17A in color with branches about 1 mm in length and recurved, ovary is 1 mm in length, 1 mm in width, inferior, and 200B in color.

*Androcoecium.*—5 stamens, fused into tube surrounding style, 2 mm in length and 0.5 mm in width, about 200A in color, no pollen was observed.

*Fruit/seed.*—Seed pods; oblong in shape, slightly curved with narrow wings, about 8.5 mm in length and 3 mm in width, a blend of 199A and 200A in color, seeds; 20 to 30 per pod, about 4.5 mm in length and 1.5 mm in width, 200A in color.

It is claimed:

1. A new and distinct cultivar of *Coreopsis* plant named 'Electric Avenue' as herein illustrated and described.

* * * * *